(12) United States Patent
Wu

(10) Patent No.: US 6,608,276 B2
(45) Date of Patent: Aug. 19, 2003

(54) APPARATUS FOR HEATING A SMALL AREA OF AN OBJECT TO A HIGH TEMPERATURE AND FOR ACCURATELY MAINTAINING THIS TEMPERATURE

(75) Inventor: Qi Wu, Eaton Town, NJ (US)

(73) Assignee: Corning Incorporated, Corning, NY (US)

(*) Notice: Subject to any disclaimer, the term of this patent is extended or adjusted under 35 U.S.C. 154(b) by 0 days.

(21) Appl. No.: 09/822,153

(22) Filed: Mar. 30, 2001

(65) Prior Publication Data

US 2003/0012238 A1 Jan. 16, 2003

Related U.S. Application Data

(60) Provisional application No. 60/193,986, filed on Apr. 1, 2000.

(51) Int. Cl.[7] .............................................. B23K 26/04
(52) U.S. Cl. ........................... 219/121.62; 219/121.73; 219/121.83
(58) Field of Search ....................... 219/121.62, 121.73, 219/121.83; 385/37

(56) References Cited

U.S. PATENT DOCUMENTS

| | | | |
|---|---|---|---|
| 4,278,867 A | | 7/1981 | Tan |
| 5,856,880 A | * | 1/1999 | Farina et al. .................. 359/43 |
| 6,356,681 B1 | * | 3/2002 | Chen et al. .................... 385/37 |

FOREIGN PATENT DOCUMENTS

| | | | |
|---|---|---|---|
| EP | 0331891 | 1/1989 | |
| EP | 331891 | * 9/1989 | ........... B23K/26/04 |
| JP | 08334645 | 12/1996 | |

OTHER PUBLICATIONS

Akiyama et al, "A novel long–period fiber grating using periodically released residue stress of pure–silica core fiber," OFC '98 Technical Digest, pp. 276–277.
Takeuchi, "Characteristics analysis of wavelength–division–multiplexing fiber couplers fabricated with a microheater," Applied Optics, vol. 35, No. 9, Mar. 20, 1996, pp. 1478–1484.

* cited by examiner

Primary Examiner—M. Alexandra Elve
(74) Attorney, Agent, or Firm—Svetlana Z. Short; James V. Suggs

(57) ABSTRACT

A heating apparatus includes: (i) a laser providing at least one beam of light capable of heating a small area of an object; (ii) a laser driver adapted to adjust optical power of this beam of light; (iii) a photo-detector adapted to detect and measure thermal radiation from the small area; and (iv) a control loop operatively linked to the laser driver and the photo-detector, the control loop providing a signal to the laser driver to adjust optical power of the beam of light based on amount thermal radiation detected by the photo-detector. According to one embodiment of the present the laser is a $CO_2$ laser and the small area is less than 0.25 mm in width. According to another embodiment it is a Nd: YAG laser.

13 Claims, 17 Drawing Sheets

APPARATUS FOR HEATING A SMALL AREA OF AN OBJECT TO A HIGH TEMPERATURE AND FOR ACCURATELY MAINTAINING THIS TEMPERATURE

CROSS-REFERENCE TO A RELATED APPLICATION

Reference is hereby made to commonly assigned patent application Ser. No. 60/193,986, filed Apr. 1, 2000 in the name of Qi Wu. and entitled "APPARATUS AND METHOD FOR HEATING A SMALL AREA OF AN OBJECT TO A HIGH TEMPERATURE AND FOR ACCURATELY MAINTAINING THIS TEMPERATURE".

FIELD OF THE INVENTION

This invention relates to a precision heating apparatus which can locally raise the temperature of objects, such as glass cane or optical fiber, to a temperature of up to 2000° C. and which has relative temperature stability of better than 0.1%. More specifically, this heating apparatus includes a laser and utilizes thermal radiation emitted from the laser-heated object to provide feedback that controls the laser power.

TECHNICAL BACKGROUND

In order to manufacture photonic components such as fused fiber couplers, and long-period gratings high temperature processing such as tapering and diffusion, for example, is required to process optical materials of these components. The selection of heat source has by far the most significant impact on these processes. For high delta (HD) germanium containing fibers, time the fiber temperature has to be raised to about 1800° C. The attributes of commonly used heat sources are compared in Table I.

Traditional heat sources have been furnace and burners. It was reported that after the burner processing fibers become brittle. Furthermore, the temperature of an open-ended furnace is limited to less than 1300° C., which requires tens of hours of diffusion time.

Resistive types of heaters, such as filament heaters, micro heaters and the induction heaters, have gained widespread acceptance in recent years for fiber processing. A distinct advantage of the resistive heaters is that the temperature can be controlled to 0.1% accuracy. However, the operating temperature is limited to less than 1700° C. by the lifetime of the resistive heater itself, and such a temperature is not high enough for diffusing germanium in a short period of time. In addition, the thermal mass in the heaters also limits the temperature rise/fall time to more than 1 minute, which may unintentionally anneal and crystallize the fiber after the thermal processing. The relatively high price of the heater coupled with their short lifetime make them the least cost-effective compared with other alternatives.

$CO_2$ lasers, by comparison, are free from these limitations. As the most widely used industry laser for more than two decades, $CO_2$ laser is highly reliable and cost-effective. Typical lifetime of a $CO_2$ laser tube is 35,000 hours or 17 years if running on a 40-hour work week basis. The laser wavelength, which is 10.6 $\mu$m, is completely absorbed by silica and glass with an absorption length of about 10 $\mu$m, making the laser beam a highly efficient heater. The "laser heater" has no thermal mass, and it is immune to the glass vapor deposition during the heating process. More importantly, the profile of the hot zone can be flexibly programmed simply by shaping or scanning the laser beam.

Despite these advantages, $CO_2$ laser has not been able to be used for manufacturing fiber based components because of a simple fact: the laser power fluctuates by about ±5%. Heating appertain that utilize $CO_2$ laser also utilize feed back loops that detect the laser power output and then change the amount of because of the small diffusion coefficient of germanium, in order to shorten the processing time the fiber temperature has to be raised to about 1800° C. The attributes of commonly used heat sources are compared in Table I.

Traditional heat sources have been furnace and burners. It was reported that after the burner processing fibers become brittle. Furthermore, the temperature of an open-ended furnace is limited to less than 1300° C., which requires tens of hours of diffusion time.

Resistive types of heaters, such as filament heaters, micro heaters and the induction heaters, have gained widespread acceptance in recent years for fiber processing. A distinct advantage of the resistive heaters is that the temperature can be controlled to 0.1% accuracy. However, the operating temperature is limited to less than 1700° C. by the lifetime of the resistive heater itself, and such a temperature is not high enough for diffusing germanium in a short period of time. In addition, the thermal mass in the heaters also limits the temperature rise/fall time to more than 1 minute, which may unintentionally anneal and crystallize the fiber after the thermal processing. The relatively high price of the heater coupled with their short lifetime make them the least cost-effective compared with other alternatives.

$CO_2$ lasers, by comparison, are free from these limitations. As the most widely used industry laser for more than two decades, $CO_2$ laser is highly reliable and cost-effective. Typical lifetime of a $CO_2$ laser tube is 35,000 hours or 17 years if running on a 40-hour work week basis. The laser wavelength, which is 10.6 $\mu$m, is completely absorbed by silica and glass with an absorption length of about 10 $\mu$m, making the laser beam a highly efficient heater. The "laser heater" has no thermal mass, and it is immune to the glass vapor deposition during the heating process. More importantly, the profile of the hot zone can be flexibly programmed simply by shaping or scanning the laser beam.

Despite these advantages, $CO_2$ laser has not been able to be used for manufacturing fiber based components because of a simple fact: the laser power fluctuates by about ±5%. Heating appertain that utilize $CO_2$ laser also utilize feed back loops that detect the laser power output and then change the amount of power to keep it to a constant level to within ±2.5%. This translates into more than 100° C. uncertainty in temperature (for a temperature of about 2000° C.), over which the fiber viscosity and diffusion rate usually change significantly.

SUMMARY OF THE INVENTION

According to an embodiment of the present invention a heating apparatus includes: (i) a laser providing at least one beam of light capable of heating a small area of an object; (ii) a laser driver adapted to adjust optical power of this beam of light; (iii) a photo-detector adapted to detect and measure thermal radiation from the small area; and (iv) a control loop operatively linked to the laser driver and the photo-detector, the control loop providing a signal to the laser driver to adjust optical power of the beam of light based on amount thermal radiation detected by the photo-detector. According to one embodiment of the present the laser is a $CO_2$ laser and the small area is less than 0.25 mm in width. According to another embodiment it is a Nd: YAG laser. According to an embodiment of the present invention a method of heating a small area of an object includes the steps of: (i) utilizing a laser to provide a laser beam characterized by its optical power; (ii) directing the laser beam onto a small area with a cross-section of less than 1 mm; (iii) heating the small area with this laser beam; (iv) detecting thermal radiation radiated from the heated area; (v) adjusting, based on the amount of detected thermal radiation, the amount of the optical power.

It is an advantage of this invention that it improves the manufactrurability of the mode field expanded "smart" fiber tapers. A second advantage of this invention is that it provides a method of the splicing specialty fiber such as Er fibers, which are widely used in amplifier modules.

For a more complete understanding of the invention, its objects and advantages refer to the following specification and to the accompanying drawings. Additional features and advantages of the invention are set forth in the detailed description, which follows.

It should be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various features and embodiments of the invention, and together with the description serve to explain the principles and operation of the invention.

SPECIFIC EMBODIMENTS

System Design

The heating apparatus of this invention utilizes at least one laser, for example a $CO_2$ or a Nd: YAG laser, and a control loop to control the laser power. Because this apparatus can locally raise the temperature of materials, such as glass and fiber up to 2000° C., and maintain the temperature stability to 0.1%, it can be used to fabricate fused fiber components and mode field expanded fiber tapers. More specifically, the heating apparatus includes: a laser providing a beam of light capable of heating a small area (of less than 1 mm) of an object (ii) a laser driver adapted to adjust optical power of this beam of light; (iii) a photo-detector that detects and measures thermal radiation from this small area; and (iv) a control loop operatively linked to the laser driver and the photo-detector. The control loop provides a signal to the laser driver to adjust and maintain optical power of the beam of light based on amount thermal radiation detected by the photo-detector.

When a fiber is illuminated by a $CO_2$ lasers beam, the equilibrium temperature is reached when the absorbed energy is balanced by the heat stored in the fiber, as well as the energy dissipated through conduction along the fiber, as well as the energy dissipated through conduction along the fiber, convection in the air, and radiation. It should be noted that a constant laser power does not guarantee a constant fiber temperature, unless the ambient temperature and airflow is tightly controlled.

As stated above, using the thermal radiation from the fiber controls the fiber temperature. At temperatures above about 1000° C., fiber material such as silica emits radiation in the visible and near-IR region, where the photo detectors such as silicon photodiodes are extremely accurate and low-cost. In GaAs photodiodes may be used to extend the detection wavelength beyond 2 $\mu$m for lower temperature regions. An array of photo detectors may also be utilized. Other alternative photo detectors are Si, In GaAs, Ge photodiodes and photo multiplier tubes (PMTs).

The strong temperature dependence of the thermal radiation power provides a sensitive indication of the fiber temperature, although the actual dependence may not be exactly $T^4$ due to the limited spectral width of the photo-detector. The voltage output from the photo detector can therefore be used to feedback control the $CO_2$ lasers, such that the voltage is locked to constant or slow-varying programmable value. The temperature stability achieved in this way is only limited by the detector noise and the stability of reference voltage source, which easily exceeds 0.1% even with a low-cost 12-bit digital to analog (D/A) card.

This temperature control method has many clear advantages. First of all, the control mechanism is insensitive to ambient conditions, this ensuring a highly reproducible process. Secondly, the control loop can be built with low-cost off-the-self components.

Experimental Implementation

Figure 1:
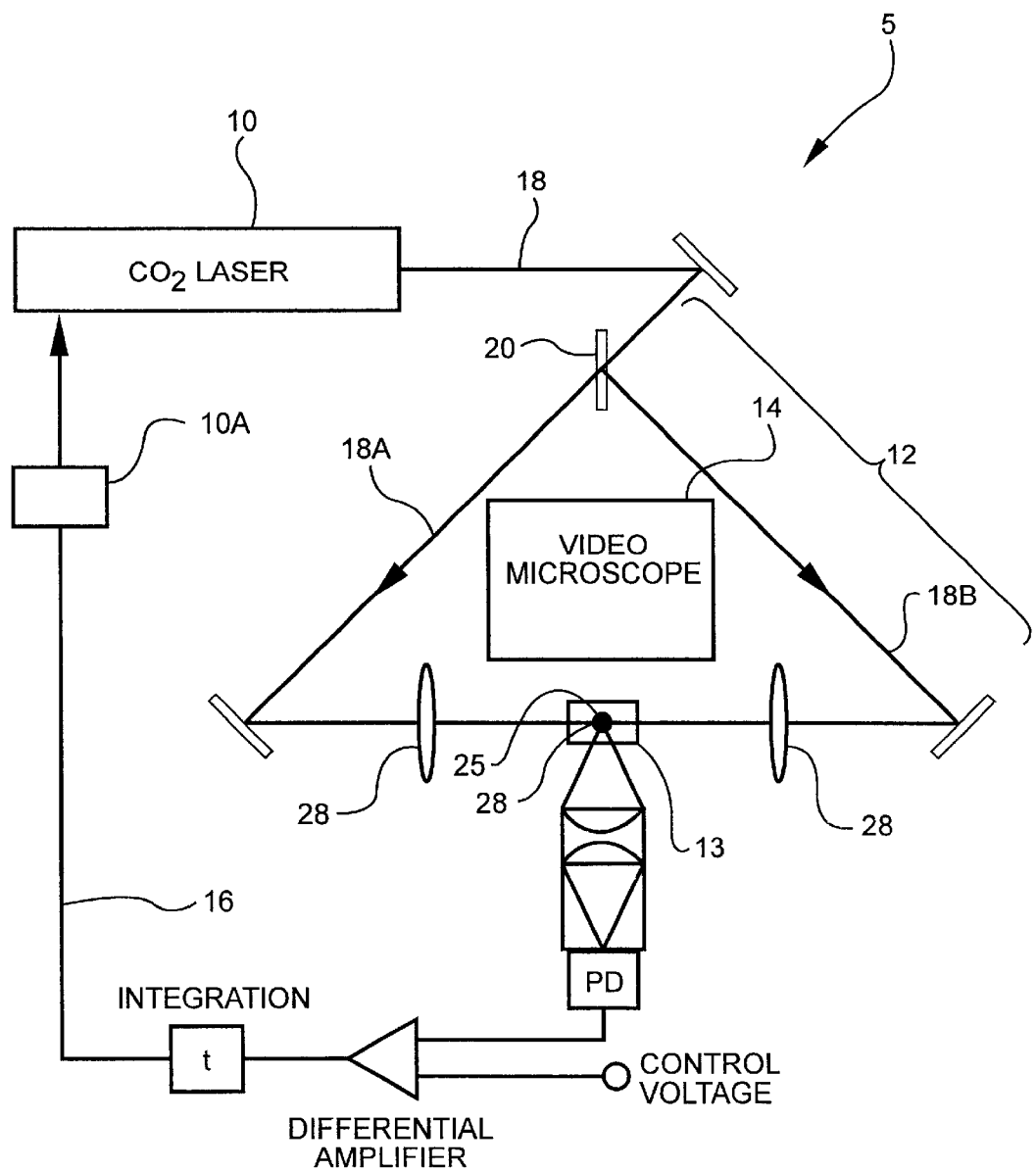
FIG. 1 is a schematic view of the exemplary heating apparatus.

The experimental setup is shown in FIG. 1. The heating apparatus 5 includes a $CO_2$ laser 10, laser driver 10A, beam delivery optics 12; a V-groove fiber holder block 13, a video monitoring system 14, and a feedback loop 16. The beam delivery optics 12 includes mirror(s), beam splitter(s),and lens(es) for example.

The $CO_2$ laser 10 utilized in this embodiment is a standard SYNRAD 25 W industry laser produced by Synrad Inc. of Mukilteo, Wash. It provides a powerful laser beam 18 with optical power that can be modulated by external voltage with kHz speed. A 50/50 ZnSe beam splitter 20 is used to equally split the laser beam into two beams 18A and 18B. These two beams are focused on the fiber 25 from opposite directions by a pair of 2 inch focal length ZnSe cylindrical lenses 28 with their optical axes aligned parallel to the fiber. No significant difference is observed when flipping the laser polarization. The reason for using two laser beams will be discussed further down in the specification.

The V-groove fiber holder block accommodates a fiber holder at a fixed and repeatable position. The V-groove has two sections, in between which is an open area to clear the laser beams. The two V-groove sections may not be perfectly aligned. Consequently micro bending may occur when the fiber is heated. We overcame this problem by first heating the fiber in a section which will be cleaved out. With the stress relieved, the fiber is maintained straight in the subsequent heating process. The stress relief process usually takes less than 30 seconds.

Figure 2:
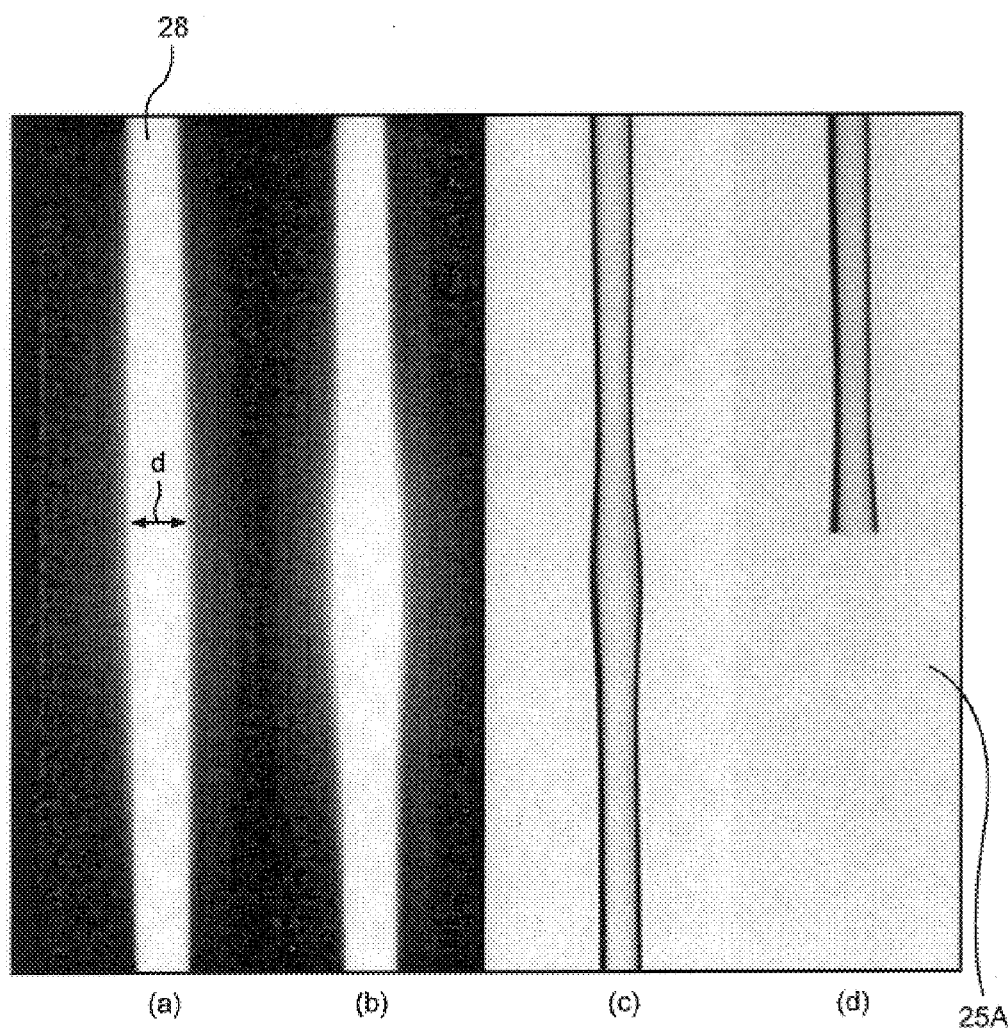
FIGS. 2a–2d illustrate the alignment of the hot zone with a cleave position.

The video monitoring system 14 monitors the position of the fiber 25 and the hot zone 28 created by the laser beam on the small area of the fiber 25. The hot zone has a cross-section width of less than 1 mm, and preferably smaller than 0.5 mm. Most preferably the width of the cross-section is less than 0.25 mm. It is preferred that this area be smaller than 1 $mm^2$, and more preferably smaller than 0.5 $mm^2$, and most preferably smaller than 0.1 $mm^2$. However, this area should be larger than 0.00005 $mm^2$. This is illustrated in FIGS. 2a and 2b.

The fiber is a cleaved fiber and has a predetermined distance from the cleaved end 25A to the tip of the fiber holder. (See FIG. 2c) This fiber is placed into the fiber holder block, with the cleaved fiber end 25A centered in the screen of the video monitoring system 14. This fiber 25, held by a fiber holder, is then stripped and cleaned before placed in the fiber holder block. When the laser 10 is turned on, the hot zone can be centered on the screen simply by steering the laser beams 18A, 18B. Once the position of the cleaved end 25A is aligned with a center of the hot zone via a video monitoring system 14, the setup can be fixed. The laser 10 is turned off and a new fiber 10 is then placed in a proper position. Then the new fiber 25 (FIG. 2d) is heated and accurately cleaved with respect to the center of the hot zone. The thermal radiation (also referred to as luminescence) is collected by a pair of low f-number lenses (i.e. lenses with f-numbers of 2 or smaller), which image the hot zone into the photo-detector such as a photodiode. Stray light (unwanted radiation) is carefully blocked to reduce false signal. In this embodiment the photodiode has an active area of 3.6×3.6 $mm^2$. The built-in trans-impedance amplifier provides a maximum gain of 1.5×$10^6$ V/A, with 50 kHz response frequency. Maximum output from the detector is 10 V, and the rms noise is less than 1 mV.

The photodiode output is compared with the reference voltage (with is referred to as "control voltage" from now on) in a differential amplifier, the error signal is integrated over the temperature response time of the fiber, and then used to correct the driving voltage of the $CO_2$ laser. The temperature rise/fall time of the fiber, which is dependent on the thermal load or the length of the hot zone, is measured to be less than 0.5 second. Alteratively the control may also be implemented in software through A/D converters. When a HP E3620A power supply (available from Hewlett Packard Company) is used as the control voltage source, the photodiode output voltage can be stabilized down to the 0.1 mV digit. The dominant noise thus comes from the photo detector itself, which is in fact further reduced by the signal averaging process. Even if we assume a 1 mV detection noise, the voltage stability is 0.1% for a photodiode output of 1 V. This corresponds to a temperature stability of 0.025%, assuming a $T^4$ dependence.

To summarize, the method of heating a small area of an object includes the steps of: (i) utilizing a laser to provide a laser beam characterized by its optical power; (ii) directing the laser beam onto a small area with a cross-section of less than 1 mm; (iii) heating the small area with the laser beam; (iv) detecting thermal radiation radiated from the heated area; and (v) adjusting, based on the amount of detected thermal radiation, the amount of said optical power. In this embodiment the laser beam is focused on the object and stray light is blocked from impinging on a photo-detector. Several different products can be made utilizing this methods. These products are, for example, a fusion splice, a plurality of fusion spliced optical fibers, a fiber lens (produced by heating an end of a optical fiber and forming it into a ball-like structure, a waveguide with an enlarged mode field diameter on one end thereof and a waveguide fused to a pigtail fiber. These products are illustrated in FIGS. 16a–16d.

Diffusion Process

The diffusion process can be generally described by the diffusion equation. For optical fibers with cylindrical symmetry, the equation can be expressed as:

$$\frac{\partial u}{\partial t} = D \left\{ \frac{\partial^2 u}{\partial r^2} + \frac{1}{r}\frac{\partial u}{\partial r} \right\} \quad (1)$$

where u(t, r) is the dopant profile as a function of time t and the radial distance r; D is the diffusion coefficient which is a function of temperature. For weakly guided single mode fiber, the dopant concentration is proportional to the index delta. Since the total amount of dopant is always a constant, the normalized frequency or V-parameter of the fiber is independent of the diffusion process. Diffusing the core dopant is thus equivalent to expanding the mode field. For simplicity, the dopant profile is approximated by a Gaussian function, which is self-consistent solution for Eq. (1). If the half widths at the 1/e maximum of the dopant profile before and after the diffusion are $r_0$ and $r_d$, respectively, the relationship between them is simply:

$$r_d^2 = r_0^2 + 4Dt \quad (2)$$

The diffusion coefficient can be expressed as:

$$D + D_0 \exp\left(-\frac{Q}{RT}\right) \quad (3)$$

where T is the temperature in Kelvin, R=8.31 J/K/mol, and the parameters $D_0$ and Q depend on the dopant and the fiber fabrication process. Literature reported $D_0$=5.7×$10^{-11}$ $m^2$/s; and Q=1.5×$10^5$ J/mol for their germanium doped fiber. From Eq. (3), the diffusion coefficient may be boosted by more than 20 times when the temperature is increased from 1300° C. to 1900° C. Although a large D is desirable in order to shorten the processing time, the fiber viscosity, which follows a similar but steeper temperature dependence as Eq. (3), places an upper limit on the processing temperature.

Control Requirements

The coupling loss between two fibers with Gaussian mode field radius of $w_1$ and $w_2$, respectively, is:

$$L = 10\log\left\{\left(\frac{2w_1 w_2}{w_1^2 + w_2^2}\right)^2 \exp\left(-\frac{2d_d^2}{w_1^2 + w_2^2}\right)\right\}$$

where d is the center offset between the two fibers. The dependence of splice loss on MFD (Mode Field Diameter) mismatch ($w_1/w_2$) is plotted in FIG. 3, assuming d=0. FIG. 4 shows a second benefit of having an expanded mode field, which can significantly reduce the coupling loss (splice loss) due to core misalignment.

Figure 3:
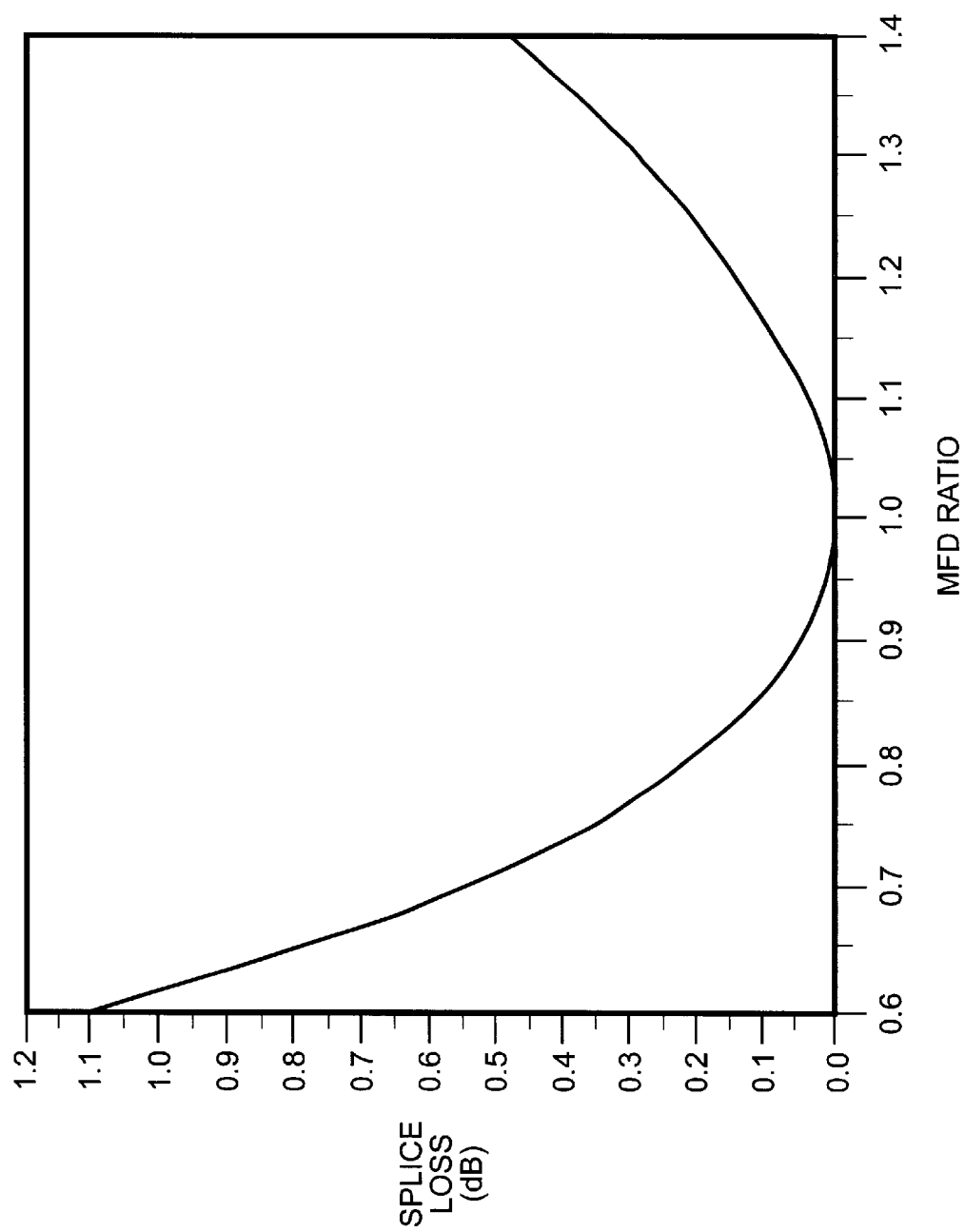
FIG. 3 is a plot illustrating the dependence of splice loss on various mode field diameters (MFD) ratio.
Figure 4:
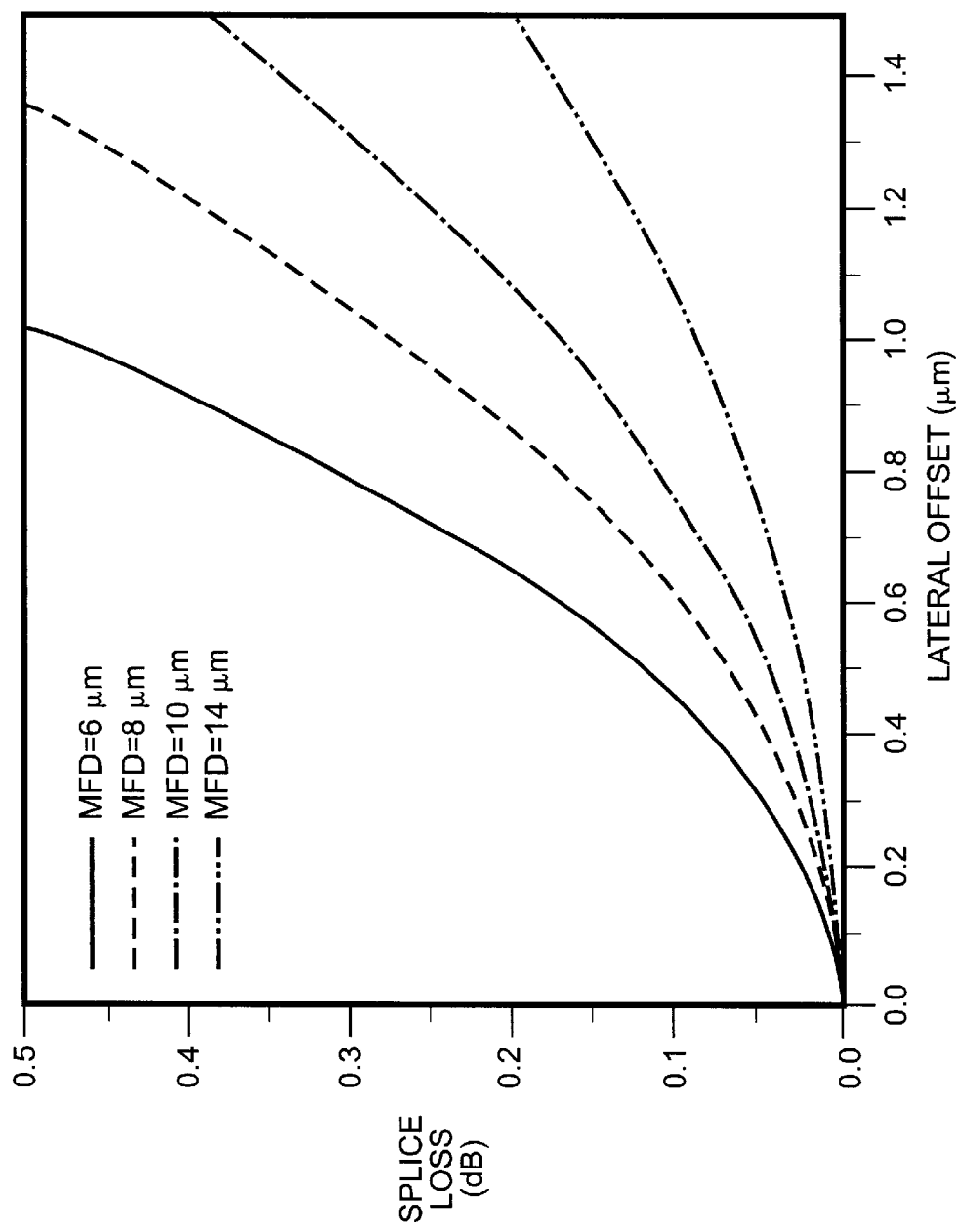
FIG. 4 is a plot illustrating the dependence of splice loss on core offset.

It appears from FIG. 3 that the mode field diameters (MFD) between the two fibers may differ by 5% while still maintaining less than 0.01 dB splice loss. However, this does not translate into the tolerance of the diffusion process, because the MFDs of fibers may have up to ±10% manufacturing error. Fiber eccentricity also contributes to the spice loss. Therefore it is desirable to limit the uncertainty contributed by the diffusion process to less than ±1%. Consider the case when $r_0 \ll r_d$, the error of MFD is dominated by that of D, with $\Delta r_d/r_d = \Delta AD/2D$. From Eq. (3), $$\frac{dD}{D} = \frac{Q}{RT}\frac{dT}{T} \quad (4)$$

Take $Q=1.5\times10^5$ J/mol, and $T\approx1600°$ C., we have $\Delta D/D \approx 10 \Delta T/T$. In other words, the temperature fluctuation is "amplified" by about 10 times in the diffusion coefficient. Many fibers have an even larger Q value, which leads to stronger temperature dependence. A temperature stability of better than 0.1% is thus essential for the diffusion process. We will discuss what this requirement implies for the laser control in the next section, but the power stability of ±5% offered by commercially available industry $CO_2$ lasers is clearly far from sufficient.

After the diffusion process, the fiber is cleaved at the diffused region. Typical $CO_2$ lasers output beam has a Gaussian profile with a full width of about 4 mm. Within 3% of the beam width from the center, the laser intensity varies less than 0.1%. The accuracy required for the cleave position is thus ±60 μm. If we further consider the heat conduction along the fiber, the uniform temperature zone may be even larger.

Figure 5:
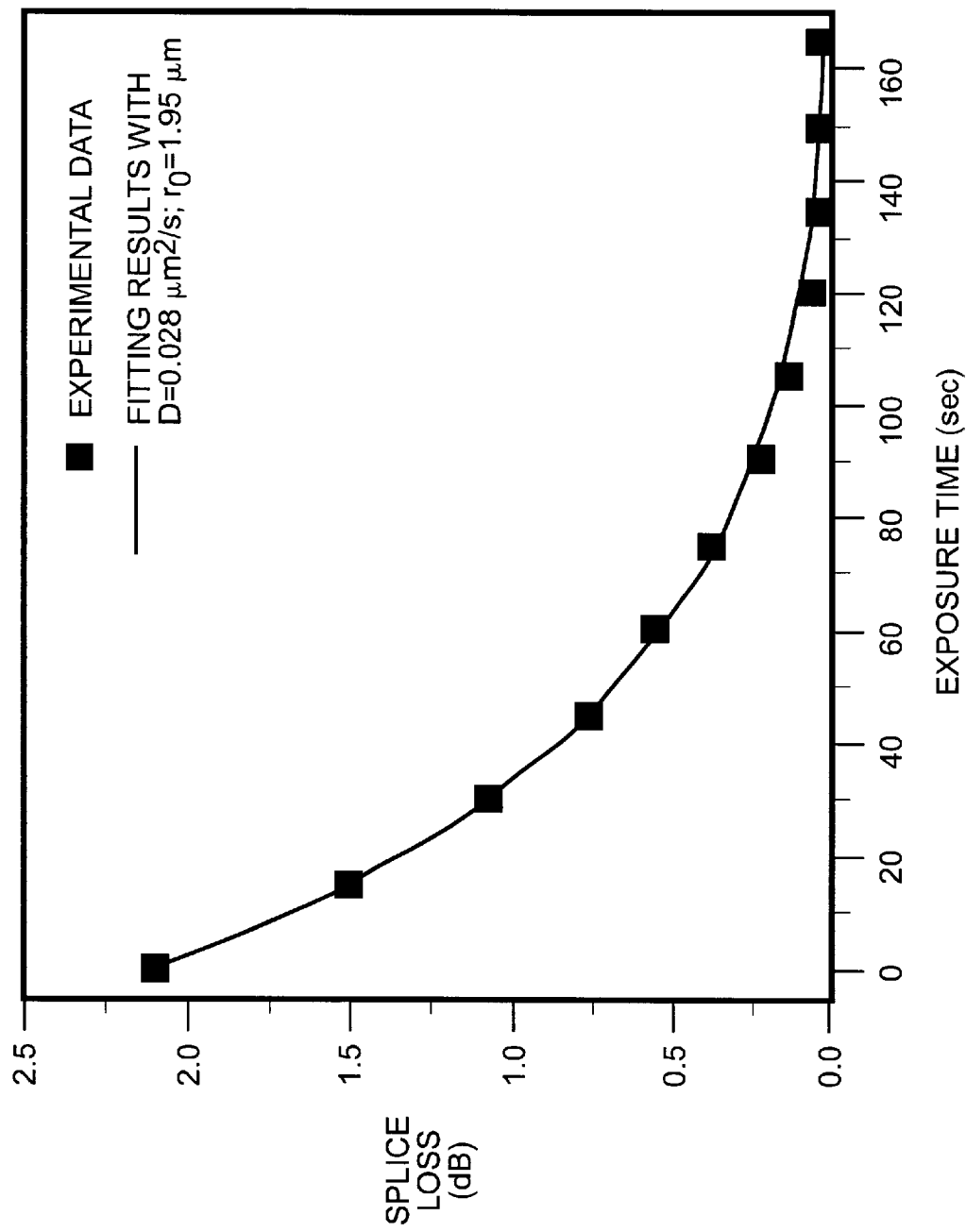
FIG. 5 is a plot illustrating splice loss as a function of exposure time.

When fusion splicing two dissimilar fibers one needs to determine an optimum heat temperature provided by the improved heating apparatus of the present invention. Because the fiber temperature is a highly sensitive parameter, we typically fix the control voltage to a predetermined value and itteratively search for the optimum exposure time. The expanded end of the HD (2% high delta) fiber is spliced to a single mode transmission fiber that is sold by Corning Inc. under the trademark name SMF-28™ using the standard single mode fiber splice recipe. FIG. 5 shows the splice loss as a function of exposure time when the control voltage is set to 1.800 V. The optimum exposure time is 150 sec, and the insertion loss is 0.04 dB. The time dependence of diffusion time can be modeled using Eqs. (2) and (4). We assume w/r=1.25, and an MFD (mode field diameter) of 10 μm for the SMF-28™ fiber. Using diffusion coefficient and the core radius of HD fiber as the fitting parameters, the curve is plotted in FIG. 5. Remarkably, the fitting is very close to the experimental data despite the crude Gaussian approximation. The initial core radius is found to be 1.95 μm. This corresponds to an MFD (of 4.9 μm, which is very consistent with the actual MFD of the HD fiber. The diffusion coefficient is found to be 0.028 μm² per second. is better than the diffusion coefficient of about 0.001 μm² per second. at 1400° C. that was reported in literature. The 28-fold increase is mainly due to the higher temperature with $CO_2$ heating.

Figure 6:
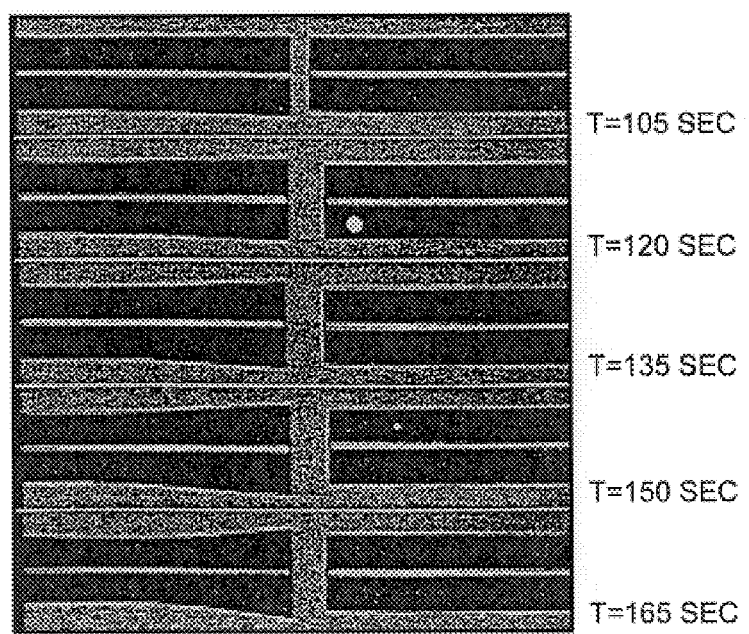
FIG. 6 illustrates cladding deformation after various amounts of exposure time.
Figure 7:
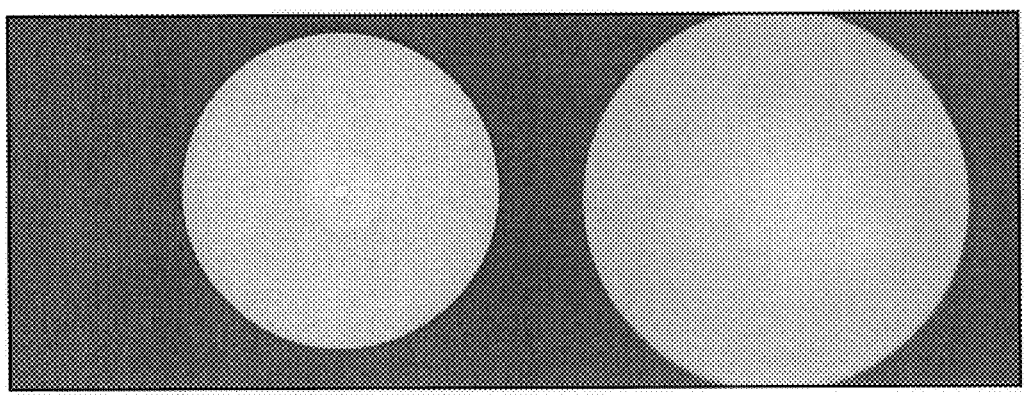
FIG. 7 illustrates cleaved end faces of high-delta (HD) fibers.
Figure 8:
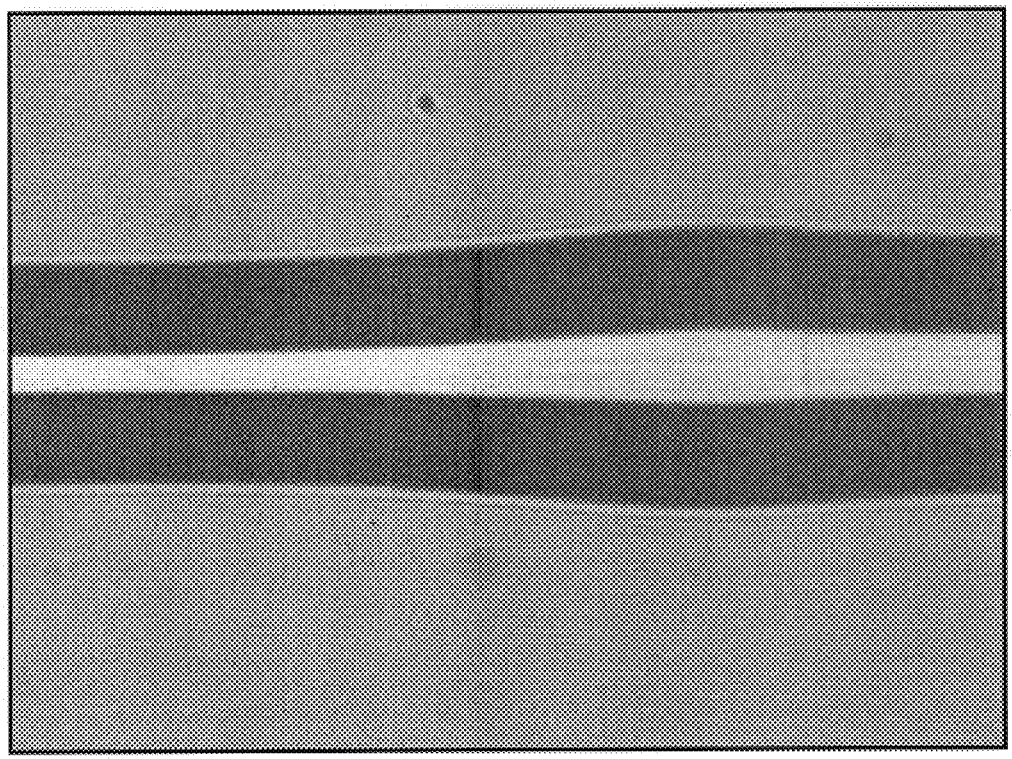
FIG. 8 illustrates a splice joint between two fibers.

Fiber deformation is visible starting from 105 sec, as shown in FIG. 6. The fiber end faces before and after the process is shown in FIG. 7, where the core is visibly enlarged after the diffusion process. The cladding diameter measures 156 μm, which results in a chipping on the cleaved end face. The cleave angle sometimes exceeds 1°. The splice loss is however not affected. The mismatch in cladding diameter does not introduce extra splice loss either, due to the very-well maintained core-clad concentricity as indicated in FIG. 7. FIG. 8 shows the splice joint. The fiber strength routinely passes 50 kpsi pull test.

Figure 9:
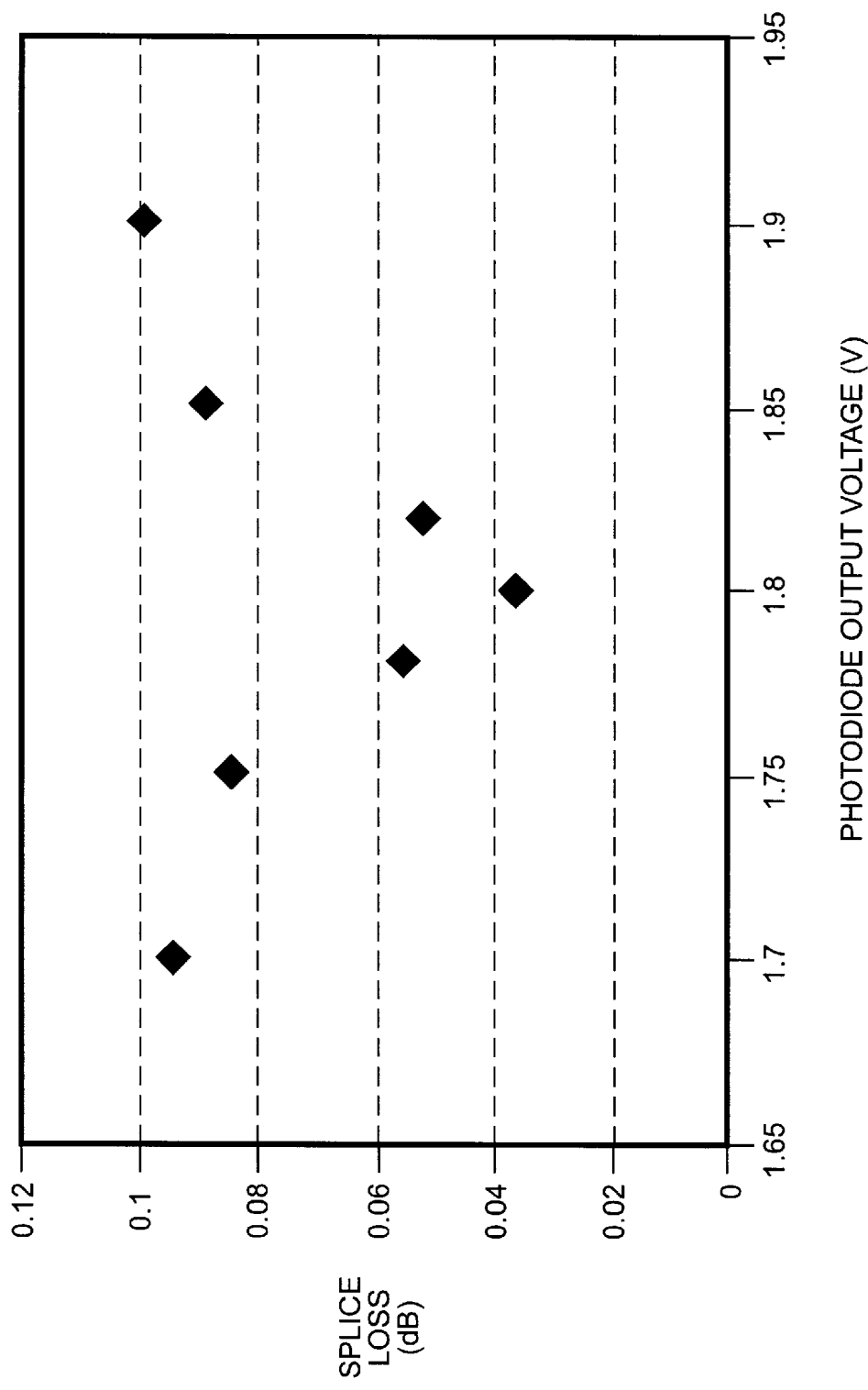
FIG. 9 is a plot illustrating the dependence of splice loss on the photodiode output voltage.

With the exposure set to 150 seconds, the splice loss is measured with varying control voltage. FIG. 9 shows the results, indicating that 1% change in the voltage, or 0.25% change in temperature, can increase the splice loss by more than 0.01 dB. The results are highly reproducible. This is consistent with our previous analysis, since 0.25% temperature change corresponds to about 1.3% change in MFD.

Figure 10:
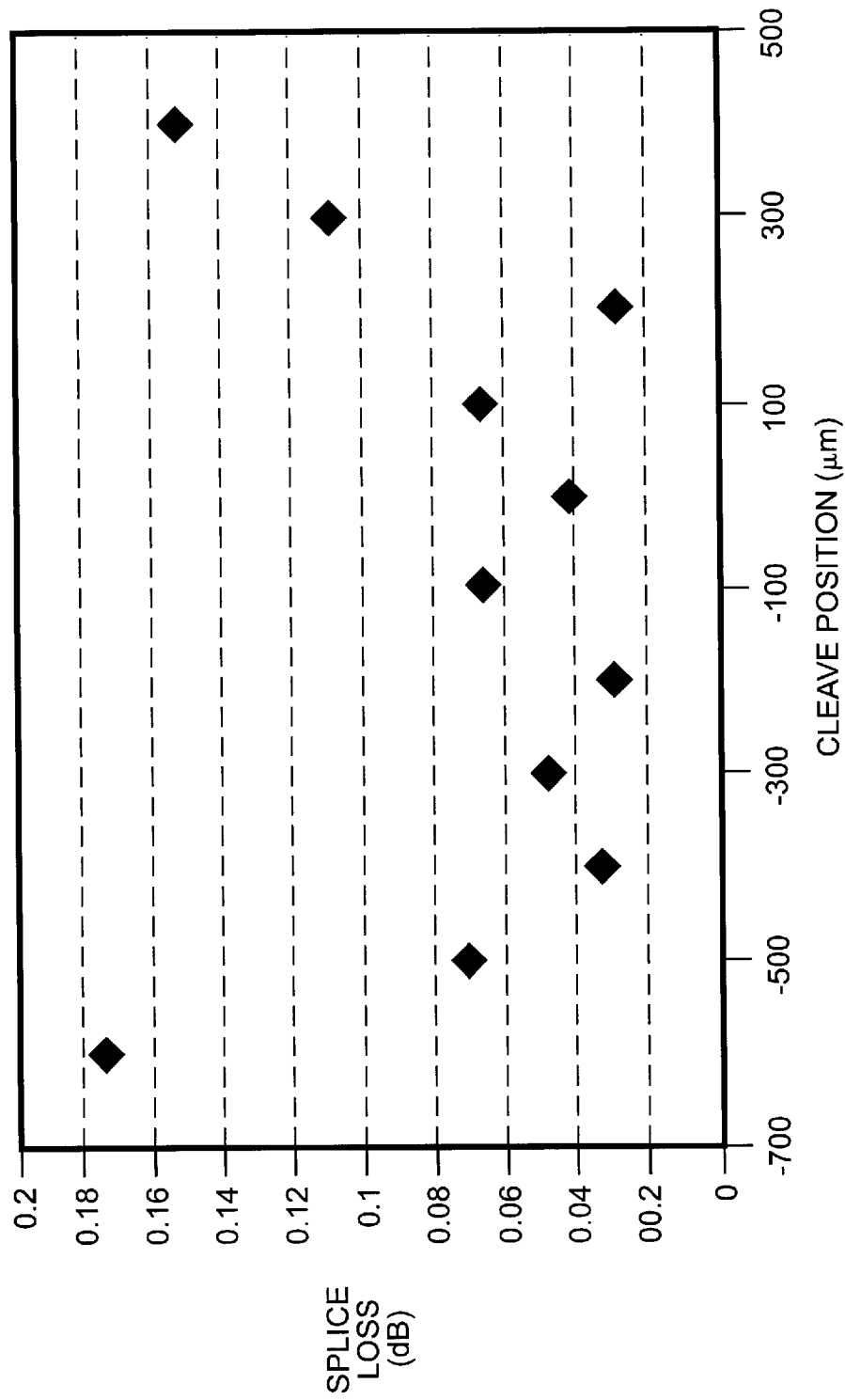
FIG. 10 is a plot illustrating the dependence of splice loss on the cleave position.
Figure 11:
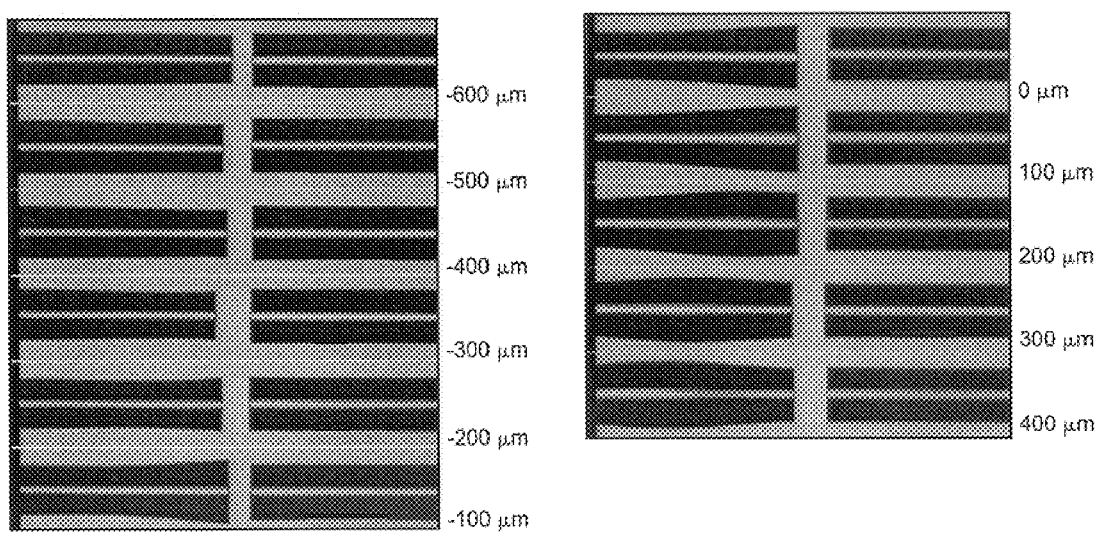
FIG. 11 provides images of mode-expanded HD fibers cleaved at various positions.
Figure 12:
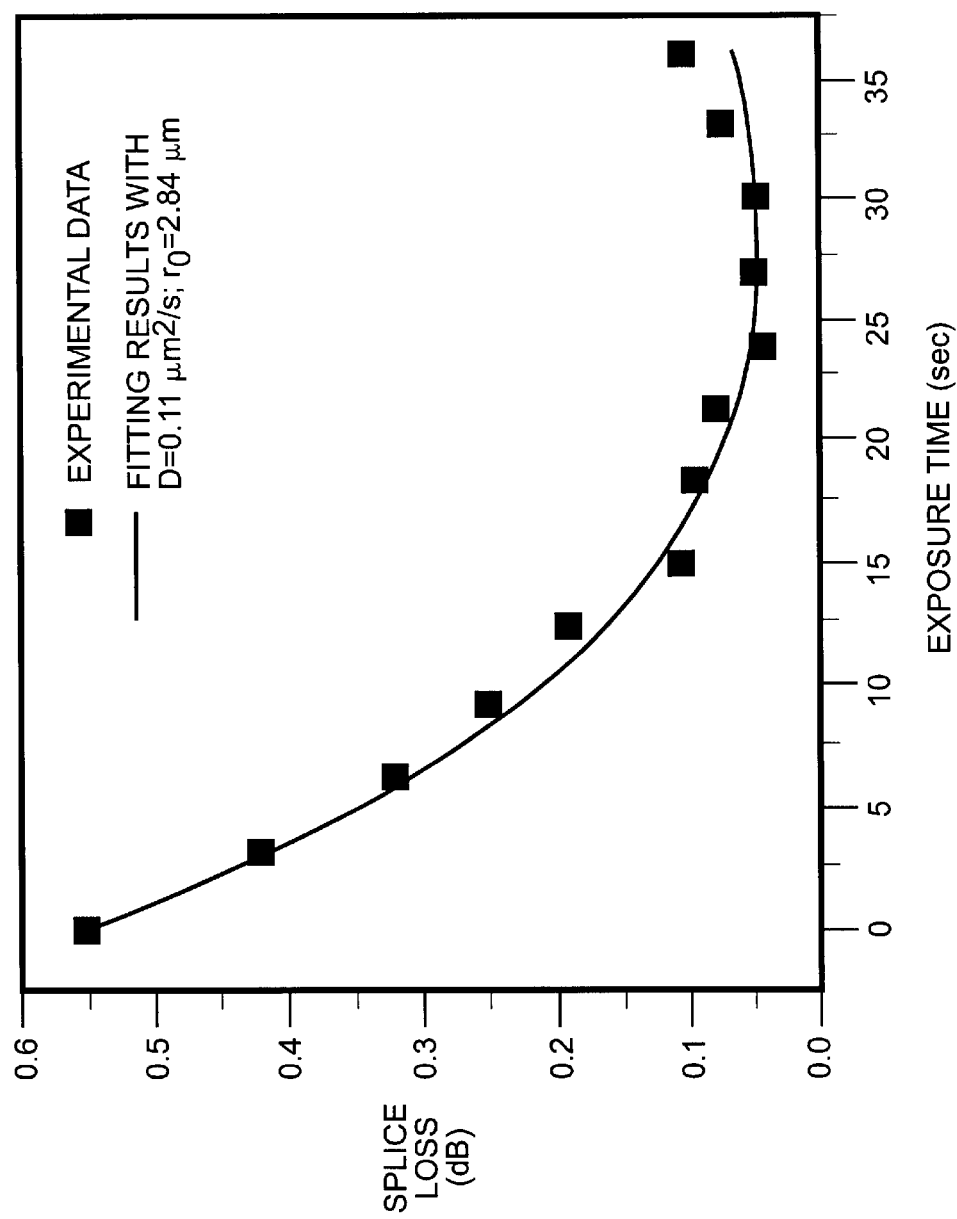
FIG. 12 is a plot illustrating the dependence of splice loss on the exposure time.

The splice loss; as a function of cleave position is shown in FIG. 10. Low splice loss is observed over a range of 600 μm, which is much larger than our estimation from the beam uniformity. The fiber images, as shown in FIG. 11, reveal that the cleaved fiber portion is down-tapered at the negative positions. The down-tapering spreads out the mode field, which explains the observed low splice loss. This effect may be used to our advantage. If we cleave at 200 μm to the right of the center of the heat zone, for example, the cladding on the end face will disappear. In fact, we found that 200 μm is indeed the optimum cleave position for splice loss and consistency.

Because the fiber viscosity is more sensitive to temperature, fiber deformation will become worse as we further reduce the exposure time. The strong deformation is in contrast to the first generation process with fusion arc, where the processing time is typically 60 seconds with comparable fiber deformation. This may be caused by the different heat profile between arc discharge and laser beam. Optimizing the laser beam size may help reduce the exposure time with minimum fiber deformation.

We attempted to measure the relation between the control voltage and the laser power. Because of the slow response of the thermal pile detector, the fiber often deforms before the power reading stabilizes, making the measurement a painstaking process. The laser power is measured to be 1.0 W and 1.2 W when the control voltage is 0.10 V and 1.80 V, respectively. Controlling the thermal luminescence is therefore intrinsically much more sensitive than controlling the laser power.

Splice loss between two dissimilar fibers, such as optical fibers CS-980™ and SMF-28™ (produced by Coming Inc.) is typically 0.15 dB when using a typical commercial arc fusion splicer. The arc time is about 15 seconds with high discharge currents in order to diffuse the germanium doped core. The long arc process wears out the electrodes rather quickly. After about 300 splices, the electrodes need to be reconditioned. This inevitably makes the splice loss inconsistent.

Figure 13:
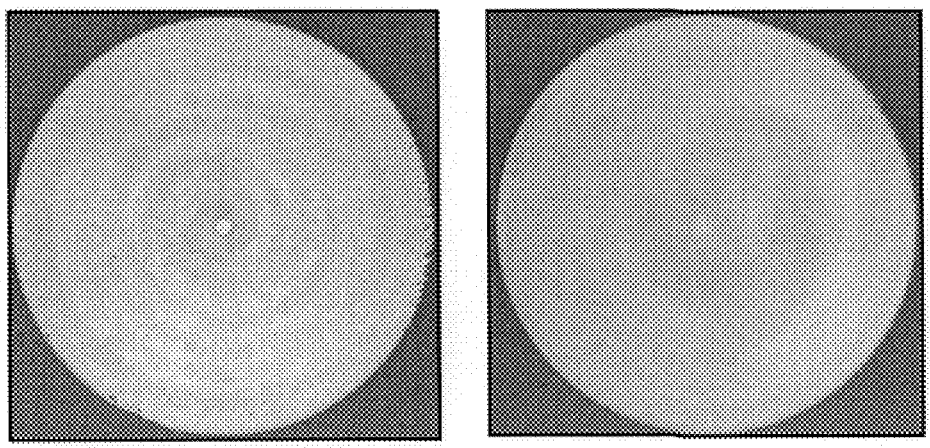
FIG. 13 illustrates cleaved end faces of other fibers.
Figure 14:
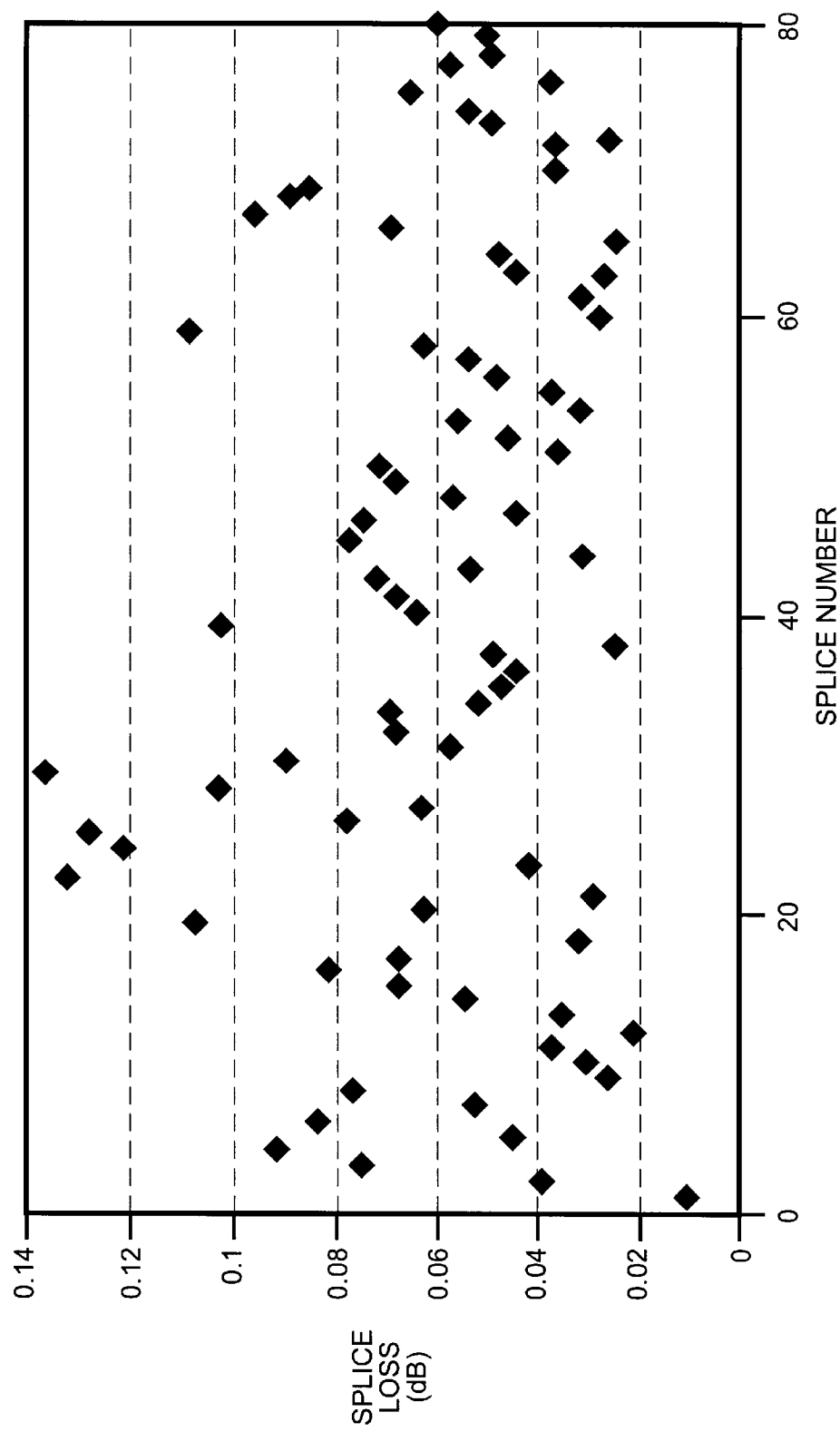
FIG. 14 is a plot illustrating the dependence of splice loss on the splice number.
Figure 15:
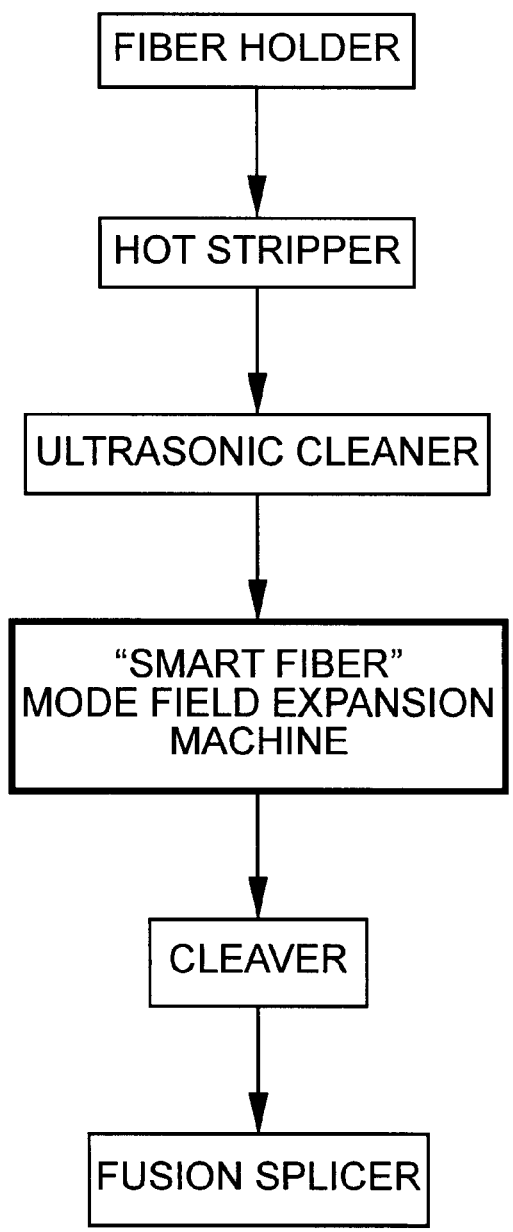
FIG. 15 is a flowchart illustrating a fusion splice process.
Figure 16A:
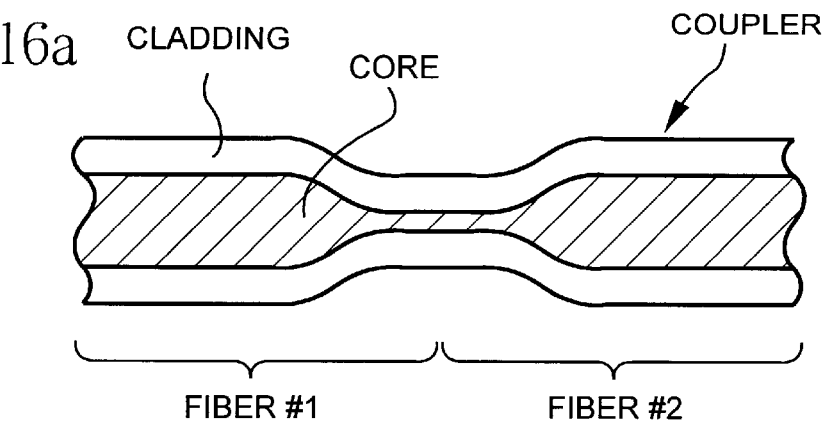
FIGS. 16a–16e illustrate some exemplary optical components manufactured by the manufacturing method of present invention.
Figure 16B:
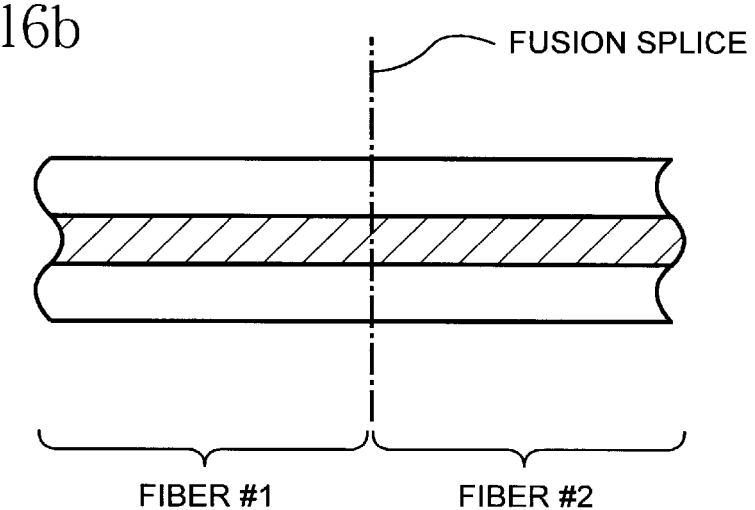
Figure 16C:
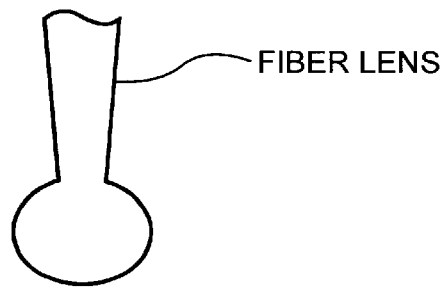
Figure 16D:
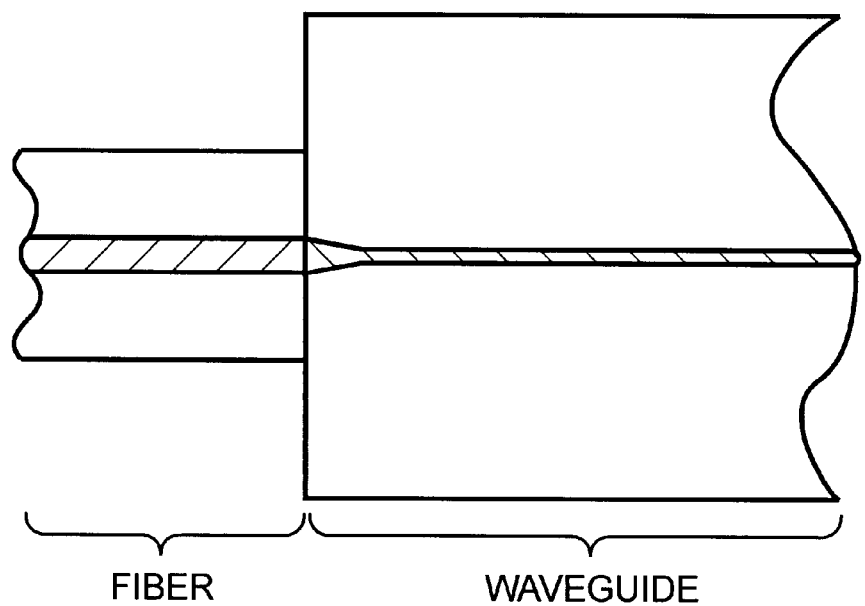
Figure 16E:
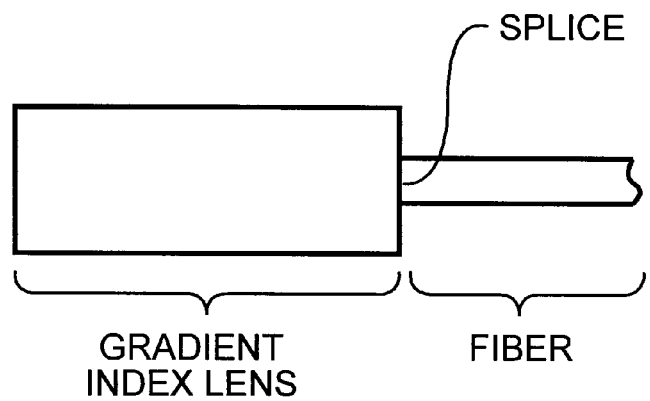

Because Corning's CS-980™ fiber only has a 1% index delta defined as $(N_{core}-N_{cladding})/Nc_{cladding}$, a relatively faster diffusion is expected. We again use the standard single mode fiber splice recipe for splicing the mode field expanded fibers, such as Corning's CS-980™ to SMF-28™ fibers. The splice loss as a function of exposure time is shown in FIG. 13, with a minimum loss of 0.06 dB. The results are reproducible within an error of 0.01 dB. There is no cladding deformation after the processing, as indicated in FIG. 14.

The time dependence of splice loss is again fitted using Eqs. (2) and (4), the fitting parameters are found to be D=0.11 $\mu m^2$ per second, and $r_0$=2.84 $\mu m$, which corresponds to an initial MFD of 7.1 $\mu m$. Compared to the HD fiber, the diffusion coefficient is 4 times higher. We believe the actual difference is smaller. This is because we assumed a Gaussian index profile, which has a smaller gradient than the actual step profile. The diffusion coefficient appears larger if we insist on a Gaussian profile. Clearly, the smaller the $r_0$, the better the Gaussian approximation. The fusion splicer also slightly expands the MFDs of both fibers.

The residual splice loss of 0.06 dB may be caused by a slight mode-field profile mismatch. We will continue to improve the process for lower splice loss even through current improvement has been satisfying.

This process demonstrates many significant advantages. First, the system is simple to operate, and rarely requires service. Second, the splice yield is exceptional due to the robust control mechanism. Finally, the entire process does not require insertion loss monitoring, which is highly desirable for manufacturing environments.

In general, this improved process can reduce the splice loss and improve the process capability of dissimilar fiber splices, which normally require a long arc discharge time with conventional fusion splicers. The splice loss will be minimum because of the "smart fiber" approach. The $CO_2$ laser and our improved control technique ensure robustness and reproducibility.

We are identifying the splices, which will benefit from this process. The spliced fibers include, for example, the following fibers produced by Corning Inc.: CS-980™ fiber to SMF-28™ fiber; CS-980™ fiber to EDF (erbium doped fiber); EDF to SMF-28™fiber; and Flexcore™ fiber to SMF-980™ fiber.

With this device the mode field expansion process may be employed to improve the coupling efficiency for micro optics, planner waveguides, and multicore fiber devices.

The present invention can be utilized to provide a robust mode field expansion process for fusion splicing dissimilar specialty fibers. Extremely accurate temperature control is achieved with a $CO_2$ laser using a novel control technique. The process generally applies to fiber splices, which normally require a long arc discharge time. Both splice loss and yield can be significantly improved with this process. By applying this process, we have consistently achieved less than 0.05 dB splice loss between the HD and SMF-28™ fibers. We have consistently reduced the CS-980™ to SMF-28™ fiber splice loss from 0.15 dB to 0.06 dB.

Thus, it is intended that the present invention cover the modifications and adaptations of this invention, provided they come within the scope of the appended claims and their equivalents.

TABLE I

Comparison of various heat sources for diffusion and fused fiber processes.

| | Temperature range | Temperature stability | Thermal mass | Hot zone length | Position stability | Life-time (hrs) | Fiber strength | Cost |
|---|---|---|---|---|---|---|---|---|
| Gas burner | >300° C. | Subject to turbulence | minimum | >5 mm | Subject to turbulence | ~3,000 | poor | low |
| Furnace | <1300° C. | ~1° C. | High | >100 mm | Good | N/A | fair | low |
| Arc discharge | >600° C. | ~1° C. | minimum | ~0.5 mm | Depends on electrode wear | ~1 (current dependent) | good | low |
| Resistive/inductive heater | <1700° C. | ~1° C. | medium | >20 mm | Good | 380 (@ 1600° C.) | good | high |
| CO2 laser | >100° C. | ??? | minimum | 0.1~20 mm | Good | 35,000 | good | Low ($4,000) |

What is claimed is:

1. A heating apparatus for heating an object, the heating apparatus comprising:
   (i) a laser providing at least one beam of light capable of heating a small area of the object, said small area being less than 1 mm in width;
   (ii) a laser driver adapted to adjust the optical power of said beam of light;
   (iii) a photo-detector adapted to detect and measure thermal radiation from said small area; and
   (iv) a control loop operatively linked to said laser driver and said photo-detector, said control loop providing a signal to said laser driver to adjust the optical power of said beam of light based on the amount of thermal radiation detected by said photo-detector.

2. The heating apparatus according to claim 1, wherein said laser is a $CO_2$ laser.

3. The heating apparatus according to claim 1, wherein said laser is a Nd:YAG laser.

4. The heating apparatus according to claim 1, wherein said small area is less than 0.5 mm in width.

5. The heating apparatus according to claim 1 further comprising a collection system adapted to collect radiation from a cross-sectional area of less than 1 $mm^2$.

6. The heating apparatus according to claim 5, wherein said collection system includes two lenses with F-numbers of 2 or smaller.

7. The heating apparatus of claim 1 further including support for an optical fiber.

8. The heating apparatus of claim 1 further including support for a long period grating.

9. The heating apparatus of claim 1 further including a scanning system that moves said beam of light relative to said object in order to provide heat to a different area of said object.

10. The heating apparatus of claim 1, wherein said beam of light is capable of heating said small area to a temperature between 1000° C. and 2500° C.

11. A heating apparatus comprising:
   (i) a laser providing at least one beam of light capable of heating a small area of an object, said small area that is than 1 $mm^2$;

(ii) a laser driver adapted to adjust optical power of said beam of light;

(iii) a photo-detector adapted to detect and measure thermal radiation from said small area; and (iv) a control loop operatively linked to said laser driver and said photo-detector, said control loop providing a signal to said laser driver to adjust optical power of said beam of light based on amount thermal radiation detected by said photo-detector.

12. The heating apparatus according to claim 11, wherein said small area is larger than 0.00005 mm$^2$ and smaller than 0.5 mm$^2$.

13. The heating apparatus according to claim 12, wherein said small area is smaller than 0.01 mm$^2$.

* * * * *